United States Patent [19]
Pfeiffer et al.

[11] Patent Number: 6,158,430
[45] Date of Patent: Dec. 12, 2000

[54] VENTILATOR SYSTEM FOR ONE OR MORE TREATMENT PATIENTS

[75] Inventors: Georg Pfeiffer, Djursholm; Georgios Psaros, Tullinge; Kurt Högnelid, Bromma, all of Sweden

[73] Assignee: Siemens-Elema AB, Solna, Sweden

[21] Appl. No.: 09/188,247

[22] Filed: Nov. 9, 1998

[30] Foreign Application Priority Data

Dec. 15, 1997 [SE] Sweden .................................. 9704663

[51] Int. Cl.⁷ ...................................................... A62B 9/04
[52] U.S. Cl. ................................ 128/202.27; 128/204.21
[58] Field of Search ........................ 128/204.22, 204.23, 128/204.18, 202.16, 200.24, 202.27, 204.21; 370/825.49; 600/513

[56] References Cited

U.S. PATENT DOCUMENTS

| | | | |
|---|---|---|---|
| 4,706,664 | 11/1987 | Snook et al. | 128/204.21 |
| 4,932,402 | 6/1990 | Snook et al. | 128/204.23 |
| 5,319,363 | 6/1994 | Welch et al. | |
| 5,375,604 | 12/1994 | Kelly et al. | 128/671 |
| 5,497,766 | 3/1996 | Foster et al. | 128/200.24 |
| 5,500,854 | 3/1996 | Uotila | 340/17 |
| 5,579,378 | 11/1996 | Arlinghaus, Jr. | 379/106 |
| 5,682,902 | 11/1997 | Herleikson | 128/708 |
| 5,685,314 | 11/1997 | Geheb et al. | 128/700 |
| 5,687,717 | 11/1997 | Halpern et al. | 128/630 |
| 5,689,242 | 11/1997 | Sims et al. | 340/652 |
| 5,701,883 | 12/1997 | Hete et al. | 128/204.26 |
| 5,936,539 | 8/1999 | Fuchs | 340/825.07 |

FOREIGN PATENT DOCUMENTS 0 707 825  4/1996  European Pat. Off. .
0 771 571  5/1997  European Pat. Off. .

*Primary Examiner*—Aaron J. Lewis
*Assistant Examiner*—Joseph F. Weiss
*Attorney, Agent, or Firm*—Schiff Hardin & Waite

[57] ABSTRACT

A ventilator system has at least one ventilator unit and a number of docking stations is described. Each docking station is adapted to receive the ventilator unit and comprises a communication interface adapted to be connected to a matching interface on the ventilator unit when the ventilator unit is docked in the docking station. The docking stations are arranged at different treatment sites, and the ventilator unit can be moved between different docking stations when necessary without interrupting the treatment of a patient connected to the ventilator unit. The same ventilator unit can be used throughout a complete treatment of a patient without any need of disconnecting the patient during transports, etc.

8 Claims, 1 Drawing Sheet

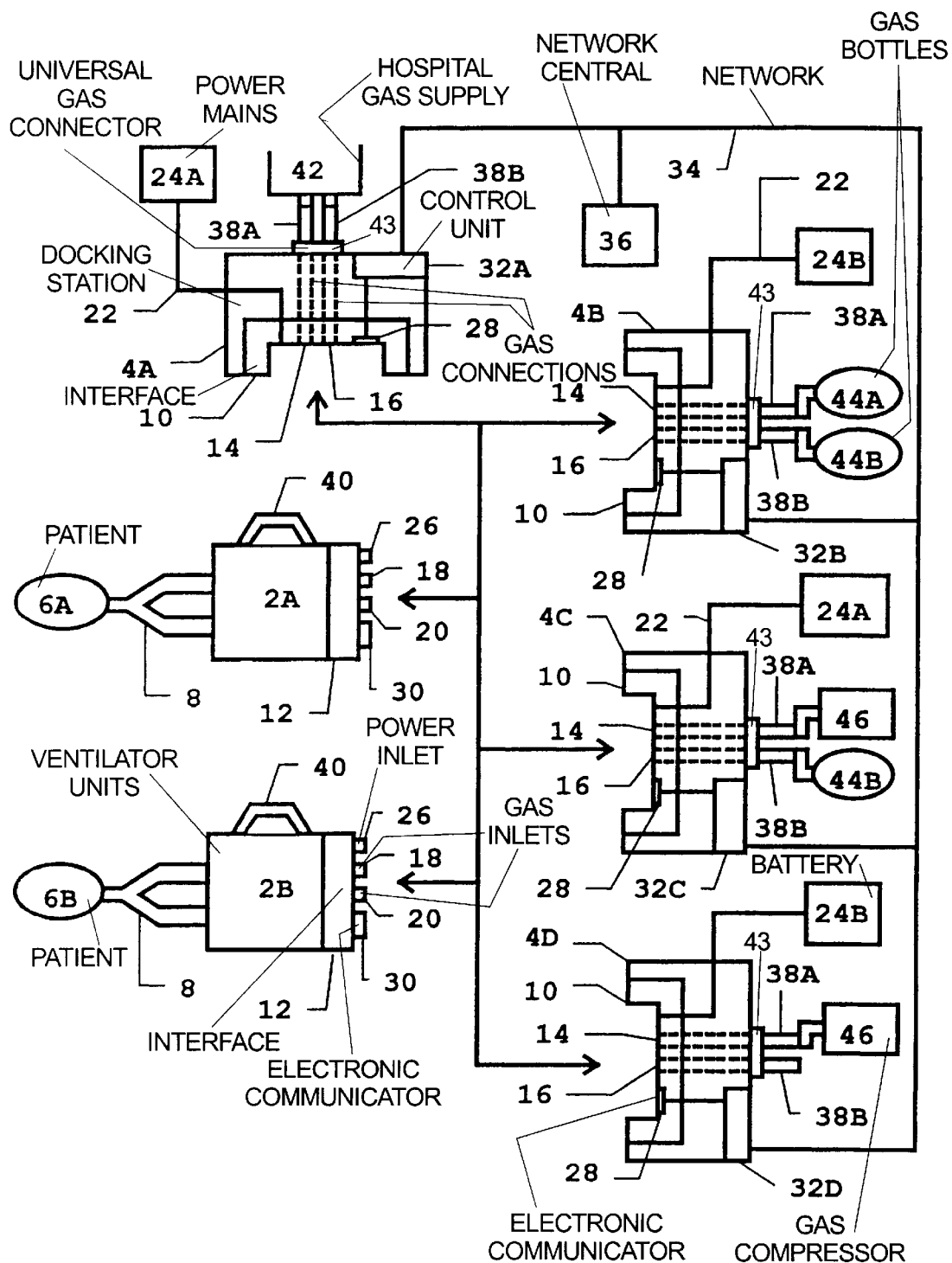

VENTILATOR SYSTEM FOR ONE OR MORE TREATMENT PATIENTS

BACKGROUND OF THE INVENTION

1. Field of the Invention

The present invention is related to a ventilator system for providing treatment to one or several subjects.

2. Description of the Prior Art

For respiratory treatment there exist today a multitude of different ventilator (respirator) devices, many of which are highly specialized for a particular treatment such as CPAP-devices or oxygenation-devices. Other devices are more flexible and can be used in intensive care, subacute care, etc. for providing a range of respiration modes. One example of latter is the Servo Ventilator 300, Siemens-Elema AB, Solna, Sweden.

The devices are either stationary, such as many devices used in intensive care, or made for transport with patients undergoing respiratory treatment. Some devices are made to be used at a patient's home, but are rarely mobile in any convenient way for the patient.

U.S. Pat. No. 5,319,363 discloses a network for portable monitoring devices. The network is basically limited to a certain number of bed-sites within a hospital, e.g. a ward. The network has fixed interfaces at the bed-sites for connection by any of a number of patient care devices. The device is brought to the bed-site and connected to the network. The device is then programmed for its particular use. Wireless communication is also possible via antennas distributed within the network area (e.g. ward). With this system a small number of devices can be used for a larger number of bed-sites.

When moving a patient, e.g. from an emergency room to intensive care, the ventilator device at the emergency room has to be disconnected. The patient is then lifted onto a trolley and connected to a transport ventilator device. In the intensive care room the patient is again disconnected, moved and connected to the ICU ventilator device. This is also the case in the network for portable devices described above, when moving a patient from one ward (or network area) to another.

All this causes discomfort to both the patient and the personnel. Every time a new device is connected to the patient, it has to be checked for functionality and set for the proper treatment. In large hospitals, devices get spread over large areas, with no control of where they are.

SUMMARY OF THE INVENTION

An object of the present invention is to provide a ventilator system that overcomes these and other problems.

This object is achieved in accordance with the present invention in a ventilator system having a ventilator unit that is adapted to be docked in one of a number of docking stations. Each docking station has a communication interface for interacting with a matching interface in the ventilator unit. By distributing the docking stations at any possible location where respiratory treatment can be needed, one single ventilator unit can follow a patient through any chain of treatment locations. The ventilator unit is simply picked up from one docking station and docked into another. When transporting, each trolley can be equipped with a docking station. Other docking stations can be placed in ambulances and helicopters.

There will thus be no need to disconnect the patient at all from the ventilator unit. In consequence, there is no need for setting and programming several devices during each transport of patient. With several ventilator units, having matching interfaces, a complete system of ventilator units and docking stations can be obtained, so that a patient basically could be moved anywhere, even between hospitals, without being disconnected from the ventilator unit.

The communication interface and matching interface can be devised so that electronic signals, treatment gases and power can be transferred between the docking station and the ventilator unit. Electronic signals and exhaled gases can be transferred between the ventilator unit and the docking station. The interfaces then have the necessary plugs and valves to avoid any leakage of gas.

All docking stations can be connected to a network, either a network solely for the docking stations, or to a hospital network. Mobile docking stations are equipped with wireless communicators for connection to the network. The location of the ventilator unit can be determined at all times. When several ventilator units are being used, they each have individual identifiers and transfer identification information to the network via the docking stations. Also, all patient and program information in the ventilator unit can be transferred to the network.

The docking stations can also include specific programming for the ventilator unit, which programming correlates to any specific requirement in the environment of the docking station (e. g. whether the docking station is located in an ICU). The operating parameters of the ventilator unit can then be adapted to certain conditions or requirements pertaining for that docking station (e.g. whether $CO_2$-measurements or respiratory gas volume calculations should be made).

DESCRIPTION OF THE DRAWINGS

The single figure is a schematic block diagram of an embodiment of a ventilator system constructed and operating in accordance with the principles of the present invention.

DESCRIPTION OF THE PREFERRED EMBODIMENTS

The ventilator system shown in the figure represents one possible arrangement of interacting devices. The ventilator system includes a first ventilator unit 2A and a second ventilator unit 2B. Each ventilator unit 2A, 2B can be connected to any of a first docking station 4A, a second docking station 4B, a third docking station 4C and a fourth docking station 4D. The ventilator units 2A, 2B can also be connected to a first patient 6A and second patient 6B, respectively. The patients 6A, 6B are connected to the ventilator units 2A, 2B via tube systems 8 (since the tube system can be identical, the same reference numeral has been used).

In the following description, it should be noted that the same elements have identical reference numbers. This, however, does not mean that they must be structurally identical. The docking stations 4A, 4B, 4C, 4D have a communication interface 10, which is adapted to receive a matching interface 12 of the ventilator units 2A, 2B. In the communication interface 10, there are gas connections 14, 16, a power line 22 and a first electronic communicator 28, each adapted for corresponding gas inlets 18, 20, a power inlet 26 and a second electronic communicator 30 in the matching interface 12.

The power line 22 thus provides the docked ventilator unit 2A, 2B with power from a power source. The power source could be a battery 24B, power mains 24A, an electric generator or any other source of power, depending on the location of the docking station 4A, 4B, 4C, 4D.

The gas connections 14, 16 are connected to a suitable gas source. In the figure, a fixed hospital gas supply system 42 and separate gas containers 44A, 44B for pressurized air and oxygen are shown which are connectable to gas ports 38A and 38B of each ventilator unit 2A, 2B. There is also shown a compressor 46 (e. g. a fan, a pump, or a turbine) as a source of pressurized air. Other known gas sources can also be used for which purpose each docking station 4A–4D has a universal gas connector 43.

The first and second electronic communicators 28, 30 can transfer any type of information between the ventilator units 2A, 2B and docking stations 4A, 4B, 4C, 4D. In particular, information regarding the identity of the ventilator unit 2A, 2B and information regarding the treatment of the patient 6A, 6B (e. g. set mode of operation, set parameters for that mode, measured parameters relating to patient, etc.) and is transferred to the docking station 4A, 4B, 4C, 4D. From the docking station 4A, 4B, 4C, 4D, specific programming can be transferred to the ventilator unit 2A, 2B, pertaining to special requirements or circumstances on site.

For this purpose, the docking stations 4A, 4B, 4C, 4D have respective control units 32A, 32B, 32C, 32D, containing specific information or programming necessary for the associated docking station 4A, 4B, 4C or 4D.

The ventilator units 2A, 2B can have handles 40 for easy change from one docking station to another.

Each docking station 4A, 4B, 4C, 4D is also connected to a network, as illustrated with line 34 and network central 36 in the figure. The configuration of the network can be made in several ways. It could be a local network only including the docking stations 4A, 4B, 4C, 4D, but it could also be part of a larger network including other devices, such as monitors, etc.

Any docking station 4A, 4B, 4C, 4D which is not stationary or does not have a physical connection with the network has the capability for wireless communication. Such combinations of networks are known, and require no further description herein. For mobile docking stations 4A, 4B, 4C, 4D, the wireless connection could also include a unit for determining the position of the transmitter (GPS or any other known system for this purpose).

Each ventilator unit 2A, 2B can have individual identifies which are transferred via the interface 10, 12 to the docking station 4A, 4B, 4C, 4D to which the ventilator unit 2A, 2B is docked. The docking station 4A, 4B, 4C, 4D then transfers this information to the network 34, 36. The location of each ventilator unit 2A, 2B can be immediately obtained at all times. This inter alia allows for optimization of the use of ventilator units 2A, 2B.

In the figure, the first docking station 4A represents all docking stations for stationary use in the hospital, such as emergency rooms, ICU's, etc. A ventilator system of the present invention thus may include a number of first docking stations 4A equal to the number of beds for stationary treatment of patients 6A, 6B.

The second docking station 4B represents all docking stations for mobile use, such as between bed sites in a hospital, transport to or between hospitals, etc. A ventilator system of the present invention thus may include a number of second docking stations 4B equal to the number of trolleys and ambulances for mobile treatment of patients 6A, 6B.

The third and fourth docking station 4C, 4D represents docking stations for stationary or mobile subacute use in hospital or in the patient's home.

Even if a patient 6A, 6B is connected to one and the same ventilator unit 2A, 2B during a complete treatment (including transport between several different docking stations 4A, 4B, 4C, 4D, the mode of operation and operational parameters set by the responsible medical staff will change as the patient's condition changes.

By configuring the control units 32A, 32B, 32C, 32D in the docking stations 4A, 4B, 4C, 4D appropriately, these can contain most of the required hardware and software for the operation of the ventilator units 2A, 2B. This provides for the possibility of specializing the control units 32A, 32B, 32C, 32D to their particular location. An ICU ventilator unit needs to be more complex than a home care or subacute ventilator. Specialization of different control units 32A, 32B, 32C, 32D makes it possible to reduce the size and weight of both ventilator units 2A, 2B and docking stations 4A, 4B, 4C, 4D intended for subacute or mobile use. Further specialization is possible by transferring more of hardware and soft ware to the network. A proper balance should be made to ensure patients' safety at all times.

In this manner, the ventilator units 2A, 2B and (mobile) docking stations 4A, 4B, 4C, 4D can be made small and light, without losing the advantages of the described system.

Even though the figure describes the ventilator system according to the invention with a multitude of possibilities, simpler systems are possible. For instance, the interfaces 10, 12 can be made for gas transport only, or gas transport and power supply, or electronic communication only, or any other combination.

Further alternatives are also possible. The interfaces 10, 12 could also include connections for transferring exhaled gas from the patient to the docking station (for further transport to evacuation or ambient, with or without purification).

The ventilator system can be configured to be additionally controlled in relation to e. g. blood gas measurements ($O_2$ saturation, partial pressure of $O_2$ or $CO_2$, etc.) ECG or EEG measurements made on the patients. The system could include, either separately or incorporated in ventilator units or docking stations, measurement units for determining lung mechanical parameters such as FRC, compliance, etc.

The docking stations can also include further connections for distributing other gases or fluids than air and oxygen, e.g. NO, laughing gas, liquid or gaseous anaesthetics (whereby the docking stations and ventilator units could be used in operating theaters as well). Different ventilator units could used, having certain specific qualities for certain defined uses, e.g. anaesthesia with one ventilator unit from sedation to awakening.

Other alternatives and additions are also possible within the context of the present invention. The invention is based on the use of a plurality of docking stations with a communication interface with at least one ventilator unit having a matching interface.

We claim as our invention:

1. A ventilator system comprising:
   at least one ventilator unit, said at least one ventilator unit having a ventilator communication interface, said at least one ventilator unit being adapted for connection to a patient for treatment of a patient and containing ventilator unit components operable to provide prescribed breathing assistance to a patient;
   a plurality of docking stations each having at least one supply source, selected from the group consisting of gas supply sources and power supply sources, at least some supply sources respectively at different docking stations being of different types and having different operating conditions associated therewith, each of said docking stations being adapted for connection to said at least one ventilator unit and comprising a control unit containing information and programming for operation of said at least one ventilator at the docking station comprising the control unit dependent on the operating conditions associated with the at least one supply source at that docking station, said at least one ventilator unit when connected to that docking station, each docking station having a docking station communication interface connected to the control unit at that docking station and mateable with said ventilator communication interface, said ventilator communication interface and said docking station communication interface, when mated, said at least one ventilator unit supplying said information and programming to said ventilation unit components for operating said at least one ventilator unit to provide said prescribed breathing assistance using the operating conditions at the docking station to which the at least one ventilator unit is connected; and said docking stations being disposed at different treatment sites, spaced from each other, and said at least one ventilator unit being mobile between said docking stations without interruption of treatment of a patient connected to said at least one ventilator unit.

2. A ventilator system as claimed in claim 1 wherein said ventilator communication interface and said docking station communication interface comprise means for exchanging electronic signals.

3. A ventilator system as claimed in claim 2 further comprising a common network connected to each of said docking stations, and wherein said electronic signals contain information identifying said at least one ventilator unit for allowing identification of a current location of said at least one ventilator unit in said common network.

4. A ventilator system as claimed in claim 3 comprising a plurality of ventilator units, each of said ventilator units having unique information identifying that ventilator unit contained in the electronic signals, allowing a location of each of said plurality of ventilator units to be identified in said common network.

5. A ventilador system as claimed in claim 1 wherein said ventilator communication interface and said docking station communication interface comprise means for receiving exhaled gas from said at least one ventilator unit for evacuation of said exhaled gas through said doking station.

6. A ventilator system as claimed in claim 1 wherein each of said docking stations comprise means for connecting said docking station to any source of gas.

7. A ventilator system as claimed in claim 1 wherein each of said docking stations comprises means for connecting said docking station to a source of gas selected from the group consisting of a fixed hospital gas supply system, gas cylinders, gas compressors, and fans.

8. A ventilator system as claimed in claim 1 wherein said ventilator communication interface and said docking station communication interface comprise means for supplying power from said docking station to said ventilator unit.

* * * * *